United States Patent [19]

Mendoza

[11] Patent Number: 4,857,064
[45] Date of Patent: Aug. 15, 1989

[54] FEMININE DISPOSABLE URINATING DEVICE

[76] Inventor: Roberto Mendoza, KM 3, Carretera a Pto. Cortes Apdo 1000, San Pedro Sula, Honduras

[21] Appl. No.: 276,037

[22] Filed: Nov. 25, 1988

[51] Int. Cl.⁴ .................... A61F 5/44; A47K 11/12
[52] U.S. Cl. ................... 604/347; 4/144.2; 4/144.3; 604/355
[58] Field of Search .............. 4/114.1, 144.1; 600/29, 600/30, 31; 604/329, 346, 347, 355

[56] References Cited

U.S. PATENT DOCUMENTS

| | | | |
|---|---|---|---|
| 940,077 | 11/1909 | Sherman | 4/144.3 X |
| 3,556,102 | 1/1971 | Davis | 604/329 |
| 3,613,123 | 10/1971 | Langstrom | 4/144.1 X |
| 3,956,778 | 5/1976 | Tanaka | 4/144.1 |
| 3,995,329 | 12/1976 | Williams | 4/110 |
| 4,116,197 | 9/1978 | Bermingham | 128/286 |
| 4,305,161 | 12/1981 | Diaz | 4/144.2 |
| 4,496,355 | 1/1985 | Hall et al. | 604/327 |
| 4,531,245 | 7/1985 | Lowd et al. | 4/144.3 |
| 4,583,983 | 4/1986 | Einhorn et al. | 604/329 |
| 4,696,067 | 9/1987 | Woodward | 4/144.1 |
| 4,734,941 | 4/1988 | DeWitt et al. | 4/144.4 |
| 4,756,029 | 7/1988 | Zieve et al. | 4/144.4 |
| 4,770,657 | 9/1988 | Ellis et al. | 604/385.2 |
| 4,784,654 | 11/1988 | Beecher | 604/329 |
| 4,815,151 | 3/1989 | Ball | 4/144.3 |

FOREIGN PATENT DOCUMENTS

| | | | |
|---|---|---|---|
| 1004104 | 1/1977 | Canada | 604/329 |

*Primary Examiner*—Henry J. Recla
*Assistant Examiner*—Robert M. Fetsuga
*Attorney, Agent, or Firm*—Oltman & Flynn

[57] ABSTRACT

Feminine disposable urinating device according to the instant invention has an elongate absorbent layer, an impermeable elongate layer longer than the absorbent layer adhesively attached to one side of the absorbent layer, a partition embedded in the absorbent layer, a flexible tubular conduit having a flange at one end disposed between the partition and the absorbent layer and having the other end of the flexible conduit passing through an opening in the absorbent layer and the impermeable layer to allow urine to be discharged through the conduit, and a hip belt having a front and a rear strap attached to the respective ends of the impermeable layer for holding it in place.

7 Claims, 2 Drawing Sheets

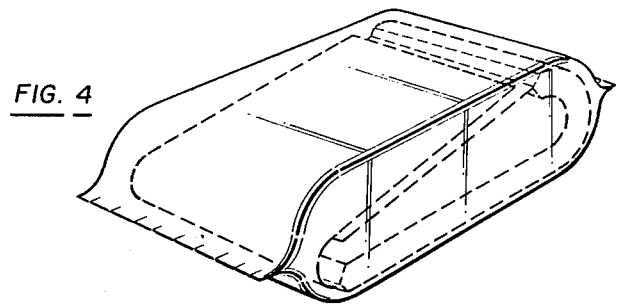
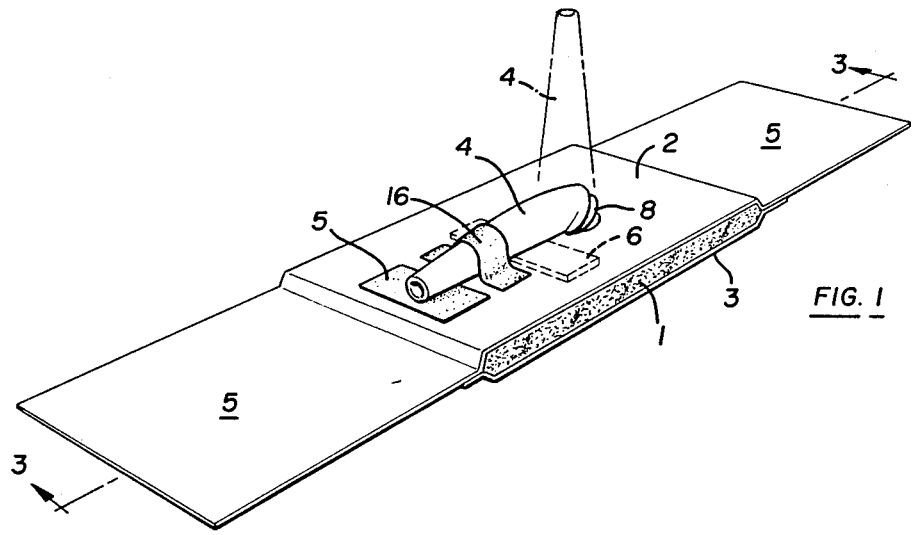
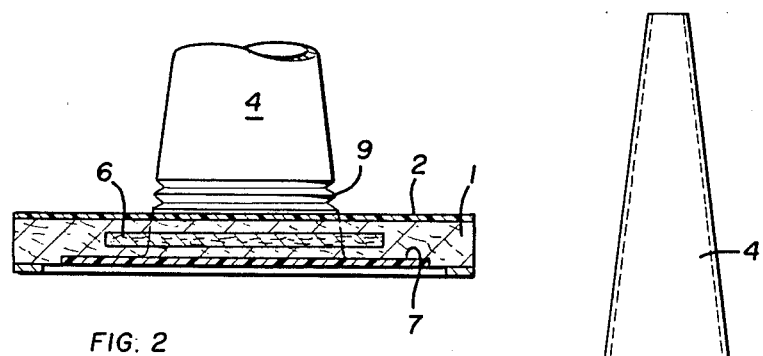
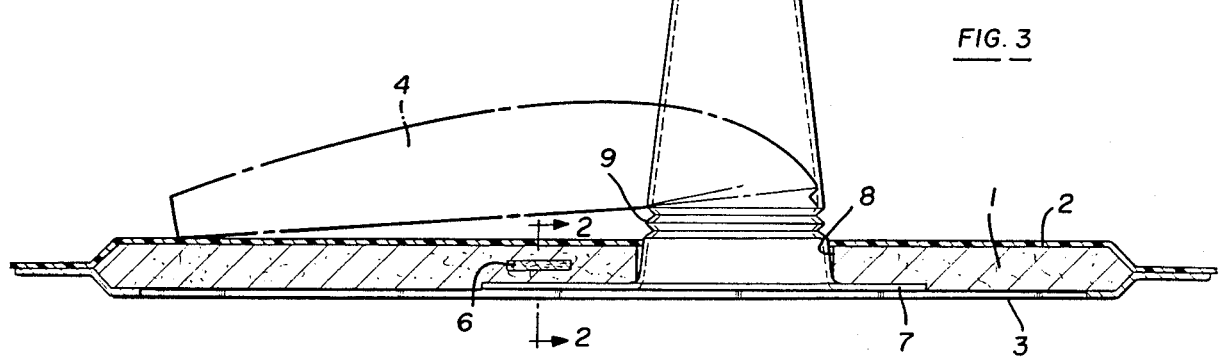

FEMININE DISPOSABLE URINATING DEVICE

The invention relates to disposable devices for aiding women in avoiding contact with toilet seats in public places.

BACKGROUND AND PRIOR ART

When women travel long distances on public busses, in airplanes, trains or automobiles, and when they visit rest rooms in public places, such as stadiums, shopping centers, etc., they frequently need to visit the bathrooms and use the toilet to discharge accumlated urine. Frequently such public places and toilets are not maintained in an acceptably sanitary and hygienic condition. For this reason, most women prefer to avoid direct physical contact with the toilet sets in such places.

Earlier devices are known which are directed to solve the problem described above. The known earlier devices, however, have disadvantages, such as exessive bulkiness or inconvenience when worn under clothing, or being inconvenient to place and operate or being inconvenient to store away.

The instant invention meets the object of overcoming the disadvantages of the known devices, in that it is capable of being worn inconspicuously without discomfort, under clothing, and needs not be stored away since it is made of inexpensive materials and is readily disposable.

SUMMARY OF THE INVENTION

The feminine disposable urinating device according to the instant invention has an elongate absorbent layer, an impermeable elongate layer longer than the absorbent layer adhesively attached to one side of the absorbent layer, a partition embedded in the absorbent layer, a flexible tubular conduit having a flange at one end disposed between the partition and the absorbent layer and having the other end of the flexible conduit passing through an opening the absorbent layer and the impermeable layer to allow urine to be discharged through the conduit, and a hip belt having a front and a rear strap attached to the respective ends of the impermeable layer for holding it in place.

In accordance with a further feature of the invention, the flexibele conduit is tapered toward the end away from the flanged end.

In accordance with still another feature, there are provided means in the form of adhesive tabs for detachbly holding the non-flanged end of the conduit folded to one side.

Other objects of this invention will appear from the following description and appended claims, reference being had to the accompanying drawings forming a part of this specification wherein like reference characters designated corresponding parts in the several views.

FIG. 1 is a perspective view of the invention showing it in flat condition.

FIG. 2 is a cross-sectional detail view of the invention showing the flanged end of the conduit.

FIG. 3 is an elevational cross-section view of the invention showing the various layers of the device.

FIG. 4 is a perspective view of the invention showing it in folded condition for compact storage.

Figure 5:
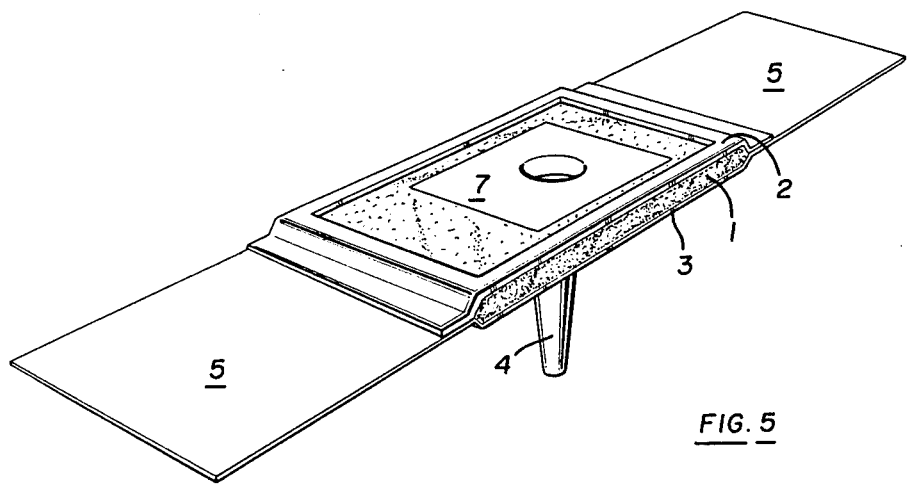
FIG. 5 is a perspective view of the invention with part of the wall broken away to show the interior construction.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation

DETAILED DESCRIPTION OF THE PREFERRED EMBODIMENTS

In FIG. 1 and 2, an absorbent layer 1 consisting advantageously of cotton or any other suitable fibrous absorbent material cast in a rectangular shape, is attached adhesively at one side of a rectangular layer of an impermeable reasonably strong plastic material being longer than the layer 3, so that two end sections 5 extend beyond the absorbent layer 1. A lining layer 3 may advantageously be adhesively attached to the othr side, i.e. the inner side of the absorbent layer 1. A circular aperture 8 is cut through the three layers to admit a tubular or cone-shaped conduit 4. The conduit 4 has at one end a flange 7, which at its outer side, facing upward in the figure, is attached adhesively to the inner side of the absorbent layer 1.

The conduit 4 may advantageously be outward tapered to a smaller diameter and have a corrugated section at its inner end which allows it to be readily bent or folded to one side as shown in FIG. 1. A relatively stiff partition 6, advantageously made of cardboard or flexible plastic is embedded in the absorbent layer 1. The purpose of the partition 6 is to induce pressure on the inferior vulva lips to urge them to remain closed in the upper part of the urine discharging orifice (urethra). In other words, it will only open to discharge into the conduit section disposed directly in front of the urinating device. This detail is shown more clearly in FIG. 6, which also shows a urinary device worn by a woman, only partially shown.

Figure 6:
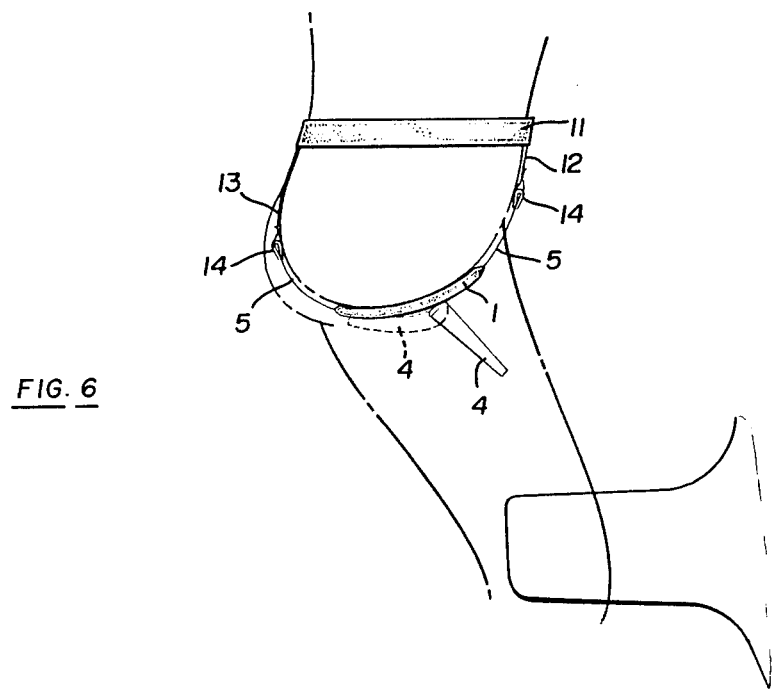
FIG. 6 is an elevational diagrammatic view of the invention showing it in use.

FIG. 6 also shows the urinating device held in place by means of a hip belt 13, having a front strap 12 attached to one end 5 of the urinating device and a rear strap 13 attached to the other end 5, i.e. the rear end, of the impermeable layer 5. Each strap 12, 13 has a clasp 14 for quick attachment to the end sections 5.

The conduit 4 is seen in FIG. 1 bent over and held in that position by means of an adhesively, yet removable, attached tab 16. An absorbent area 5, for example in the form of an opening in the impermeable layer 2, serves to absorb a small amount of urine after the use of the device, and so that urine does not come into contact with the user's clothing.

The use of the feminine disposable urinating device is easy and familiar to women because it is held in place by the hip belt, previously widely known for the use of sanitary napkins. This belt is worn over the hips and the urinating device is held in place by the metal pronged straps 12 and 13 of the elastic belt, permitting the urinating device to adjust anatomically to the body thus avoiding discomforts and problems with use. This detail is shown in FIG. 6.

A special embodiment of the invention may be constructed to permit the recollection of the urine slightly closer to the female body. In this embodiment a special hidden zipper is provided with the purpose of extracting the conduit 4 without the need of undressing. An especially thin zippered panty may be used as well, permitting this same operation from the inside. For extra comfort, the urinating device is arranged to fold up and thus form a very small package, for example 6.5 cms. wide, 9.5 cms. long and 2.5 cms. thick. This permits women to keep a couple of the folded devices in their purses while travelling or visiting public sites. The device in its folded form is seen in FIG. 4.

The instant invention facilitates the action of urinary discharge from the female bladder from a standing position in ordinary toilets and especially for women of different weights. The invention is totally different in comparison to the concepts of previous inventions.

I claim:

1. A feminine disposable urinating device comprising: an elongate impermeable layer; an elongate impermeable layer adhesively attached to the absorbent layer, and being longer than the absorbent layer, having front and rear ends extending beyond the ends of the abosrbent layer; a flexible tubular conduit having a flange at one end adhesively attached to one side of the absorbent opposite the impermeable layer, an aperture through the absorbent layer and the impermeable layer for admitting the other end of the tubular conduit; a flexible partition embedded in the absorbent layer proximal to the side of the aperture facing the rear end of the impermeable layer; and a hip belt having a front and rear strap attached to the respective front and rear end of the impermeable layer.

2. A feminine disposable urinator according to claim 1, wherein said flexible conduit is tapered toward the end facing away from the flanged end.

3. A feminine disposable urinator according to claim 1 including adhesive tabs for detachably holding the end of the flexible conduit, facing away from the flanged end, folded against the impermeable layer.

4. A feminine disposable urinator according to claim 3 having an absorbent area close to the end of the conduit as folded against the impermeable layer.

5. A feminine disposable urinator according to claim 1 having an absorbent lining adhesively attached to the side of the absorbent layer opposite the impermeable layer.

6. A feminine disposable urinator according to claim 1 wherein said flexible conduit has circular corrugations at the end proximal to the flange.

7. Device according to claim 1 including pronged clasps attached to said straps for gripping the ends of impermeable layer.

* * * * *